United States Patent [19]
Christensen et al.

[11] 3,968,101
[45] July 6, 1976

[54] 8-SUBSTITUTED CYCLIC NUCLEOTIDES BY FREE RADICAL ALKYLATION AND ACYLATION

[75] Inventors: Leon F. Christensen, Costa Mesa; Roland K. Robins, Santa Ana, both of Calif.

[73] Assignee: ICN Pharmaceuticals, Inc., Irvine, Calif.

[22] Filed: Dec. 20, 1974

[21] Appl. No.: 534,750

[52] U.S. Cl. .......................... 260/211.5 R; 424/180
[51] Int. Cl.² .......................................... C07C 19/20
[58] Field of Search ............................ 260/211.5 R

[56] References Cited
OTHER PUBLICATIONS
Kawazoe et al. "Chem. Pharm. Bull" vol. 20, pp. 1341-1342, 1972.

*Primary Examiner*—Johnnie R. Brown
*Attorney, Agent, or Firm*—Thomas Kiley; Kay H. Boswell

[57] ABSTRACT
Novel compounds of the general formula

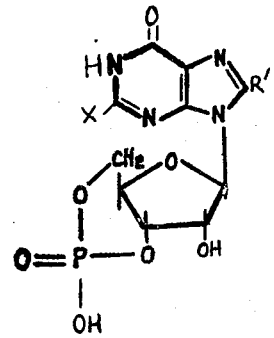

wherein X is H or $NH_2$; R' is $C_1$ to $C_8$ alkyl, $C_1$ to $C_8$ substituted alkyl, benzyl, $C_1$ to $C_8$ acyl, benzoyl, carbamoyl, are disclosed as well as a novel free radial alkylation and acylation process for making such compounds. The compounds of the invention display activity comparable to or superior to their naturally occurring analogue while resisting phosphodiesterase degradation. In some cases the compounds of this invention actually inhibit enzymatic degradation of the natural analogue.

17 Claims, No Drawings

8-SUBSTITUTED CYCLIC NUCLEOTIDES BY FREE RADICAL ALKYLATION AND ACYLATION

BACKGROUND OF THE INVENTION

As reported by Sutherland et al in "Cyclic AMP", *Am. Rev. Biochem.* 37, 149 (1968), cyclic adenosine monophosphate (C-AMP) has been established as an intracellular "second messenger", mediating many of the actions of a variety of different hormones. According to this theory, first messenger hormones, epinephrine and norepinephrine, influence adenyl cyclase contained at or within cell walls to form intracellularly cyclic AMP from adenosine triphosphate upon receipt of the extra-cellular hormone signal. The formed cyclic AMP in turn functions as a second messenger and stimulates intracellular functions particular to the target cells of the hormone. Cyclic AMP has thus been shown to "activate" certain protein kinases, which in turn produce physiological effects such as muscle contraction, glycogenolysis, steroidogenisis and lipolysis.

More recently, the biochemical functions of guanosine cyclic-3',5' phosphate has been studied. c-GMP has been suggested to be involved, like cAMP, in the cellular mediation of hormone action. A review of the literature with respect to the biochemical function of the cGMP can be found in Miller et al (1972) *Biochemistry* 12, 5310 herein incorporated by reference and hereinafter summarized. It has been observed that acetylcholine caused an elevation of myocardial cGMP levels when added to the isolated perfused heart. It was further reported that the injection of oxotremorine, a cholimimetic agent, resulted in an increase in acetylcholine in rat brain which was accompanied by a concomitant rise in cGMP levels. Atropine, an anti-cholinergic agent, prevented this increase in cGMP levels. It was demonstrated that μM 8-bromo-cGMP was able to mimic the action of the cholinergic agents, carbachol and acetylcholine. This cGMP derivative caused enhanced IgE-mediated release of histamine and of the slow reacting substance of anaphylaxis in human lung fragments. Other studies have shown the administration of acetylcholine resulted in the accumulation of cGMP in heart, brain, and ductus deferens. Finally, the effects of intraperitoneal administration of a variety of 2'-,6- and 8- substituted cAMP, cIMP (inosine cyclic 3',5' phosphate) and cGMP derivatives on blood sugar, blood corticoid levels, heart rate and blood pressure in rats has been reported.

A number of studies have suggested that the physiological action of cGMP are inverse to those of cAMP. The cAMP-stimulated synthesis of β-galactosidase in bacterial cell-free extracts was antagonized by cGMP. It has been shown that dbcGMP and cGMP decreased the rate of the beating of cultured heart cells, in contrast to the acceleration produced by cAMP. Cyclic GMP caused contraction of a rate stomach fundus strip, while increased concentrations of cAMP were associated with smooth muscle relaxation. Renal cortical cGMP levels were decreased in metabolic acidosis, and were increased in alkalosis. Although no changes in cAMP levels were seen during either acidosis or alkalosis, it has been reported that cGMP is suppressed, and cAMP stimulated, the renal cortical production of ammonia from glutamine in vitro. It was also demonstrated that cGMP was capable of labilizing the membranes of lysosomes prepared from sensitized human polymorphonuclear leukocytes, while cAMP stabilized the membrances. Studies indicate that cGMP levels were markedly elevated in the psoriatic lesion, while cAMP levels were decreased. It has also been demonstrated that cholinergic agents of cGMP enhanced the cytotoxicity of antigen-sensitive lymphocytes, while cAMP inhibited cytotoxicity. The phytohemagglutinin- or concanavalin A-induced clonal proliferation of lymphocytes produced a 10–50 fold increase in cGMP levels, while cAMP levels in the cells were essentially unaffected.

It is now well established, as supported in the literature cited in the previously referenced Miller et al article, that increased levels of cAMP are associated with reduced growth rate and induction of differentiation. The growth inhibitory effects of cAMP may be mediated in part by the inhibition of precursor transport into cells. Cyclic GMP antagonizes this inhibition. The available data suggest that cAMP limits growth, possibly by promoting differentiation, while cGMP stimulates growth at the expense of differentiation.

More recently, evidence has been presented that is consistent with the involvement of cGMP in the regulation of prostagladin synthesis and release, Stoner et al, 1973, *Proc. Nat. Acad. Sci. USA* 70, 3830.

Naturally occurring cyclic nucleotides, cAMP, cGMP and cIMP are degraded, however, in vivo by phosphodiesterase enzymes, which catalyze hydrolysis of the cyclic purine nucleotide to a 5'-monophosphate with a consequent loss of function. It has accordingly been suggested that substituted cyclic AMP, GMP and IMP analogs which are more resistant to phosphodiesterase degradation than the naturally occurring cyclic nucleotide might be administered in aid of lagging cellular processes. Another suggestion has been to enhance the beneifical effects of naturally produced cyclic nucleotides by administering compounds which are capable of inhibiting the undesirable effects of phosphodiesterase enzymes.

Sutherland et al, in *Circulation* 37, 279 (1968) suggest that the pharmacological effects of theophylline are the result of its ability to inhibit the action of phosphodiesterase enzymes. Theophylline has thus been employed in lieu of the adenyl cyclase-stimulating hormones, epinephrine and norepinephrine, as a heart stimulant following cardiac arrest and in refractory asthma cases as a bronchial dilator. Theophylline, however, does not selectively inhibit phosphodiesterase, but rather gives general stimulation to the central nervous system. Accordingly, the use of theophylline can make the recipient nervous and irritable and can also create cardiovascular effects, i.e., rapid beating. By the same token, theophylline is not as potent a phosphodiesterase inhibitor as is desired and consequently has to be used in larger quantities , which, of course, can further the undesirable effects enumerated above.

Further, due to the apparent opposite cellular effects of cGMP and cAMP, it is desirable to have a class of compounds not only capable of inhibiting phosphodiesterase enzyme, but having the ability to selectively stimulate cGMP protein kinase while not activating cAMP protein kinase.

Recently reported has been the synthesis of a number of 8-alkylthio, 8-arylthio- and 8-alkylamino-cGMP derivatives, along with 8-hydroxy-and 8-bromo-cGMP, some of which have shown the ability to selectively stimulate a purified cGMP-dependent protein kinase from lobster tail but did not activate the cAMP dependent kinase from bovine brain (Paoletti, et al, 1973, *Pharmacol. Res. Commun.* 5, 87; Miller et al, *Biochemistry* 12, 5310). Many of these compounds were, in addition, themselves resistant to hydrolysis by cyclic nucleotide phosphodiesterase.

Historically, 8-alkyl purines have been synthesized by Traube cyclization of a 4,5-diaminopyrimidine with the appropriate carboxylic acid fragment (Robins, 1967 in "Heterocyclic Compounds, Vol 8", R. C. Elderfield, Ed., Wiley, New York, N.Y., p. 162). The only 8-acyl-purine derivatives known prior to the present invention are 8-acetylcaffeine, 8-propionylcaffeine and 8-acetyl-theophylline (Ehrhard and Hennig, 1956, *Arch. Pharm.* 289, 453), prepared from 8-cyanocaffeine and 8-(1-hydroxyethyl) theophylline, respectively. For the purpose of synthesizing 8-substituted compounds capable of selectively stimulating protein kinase, while resisting and inhibiting phosphodiesterase enzyme reactions, it is desirable to develop methods of introduction of alkyl and acyl groups directly onto existing guanosine 3',5'-cyclic phosphate molecules.

Homolytic alkylation and acylation of heterocyclic system has only recently appeared. Kawazoe, et al, 1972, *Chem. Pharm. Bull.* 20, 1341, have examined homolytic free radical methylation of guanine, guanosine, and 5'-guanylic acid and found that 8-methylguanine was produced from the action of guanine and t-butyl hydroperoxide, $FeSO_4$, in the presence of dilute sulfuric acid.

However, there has been no reported synthesis of 8-substituted alkyl or acyl 3',5'-cyclic nucleotides via this method. As previously mentioned, 8-alkyl purines have in the past been synthesized via a Traube cyclization while the few 8-acyl purines synthesized thus far has been accomplished via substitution of other 8-substituted compounds as opposed to direct substitution onto the heterocyclic ring. Where direct substitution to obtain 8-substituted purines has been accomplished, it has been by a nucleophilic or electrophilic displacement reaction.

For example, Robins et al, Ser. No. 474,923, filed May 31, 1974, now abandoned "6,8-Disubstituted-9β-D-Ribofuranosylpurine 3',5'-Cyclic Phosphates", assigned to the same assignee as the present invention, teaches direct nucleophilic or electrophilic substitution of various 3',5' cyclic phosphate nucleotide purine derivatives at the 8 position with such groups as halogens, hydroxyls or amines which readily undergo nucleophilic or electrophilic substitution.

SUMMARY OF THE INVENTION

We now wish to report the synthesis of a novel class of cGMP and cIMP analogs, i.e., 8-alkyl and 8-acyl-cGMP and cIMP derivatives, which act as activators of cGMP dependent protein kinases and as substrates and inhibitors of phosphodiesterases. The novel homolytic alkylation and acylation procedures employed in the synthesis of these compounds provides a direct method of alkylating and acylating the 8-position.

More particularly, disclosed are compounds of the general formula:

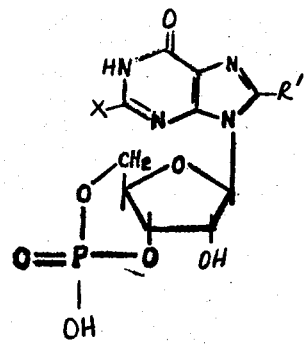

wherein X is H or $NH_2$; R' is $C_1$ to $C_8$ alkyl, $C_1$ to $C_8$ substituted alkyl, benzyl, $C_1$ to $C_8$ acyl, benzoyl and carbamyl, and a novel synthesis process for producing such compounds.

PREFERRED EMBODIMENT

The following reaction scheme for the alkylation and acylation of cGMP and cIMP is given.

REACTION SCHEME

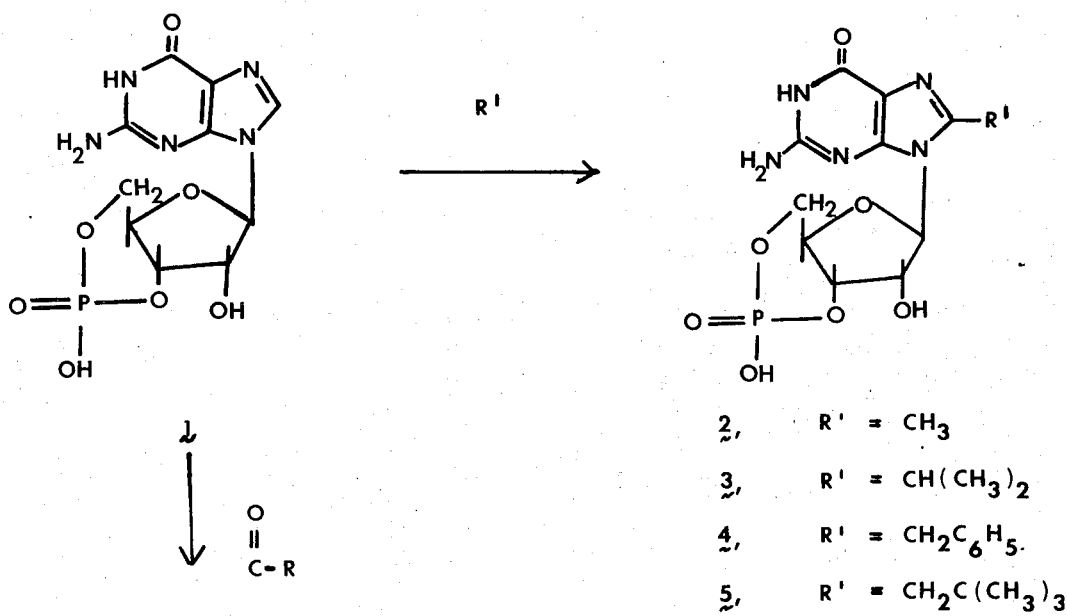

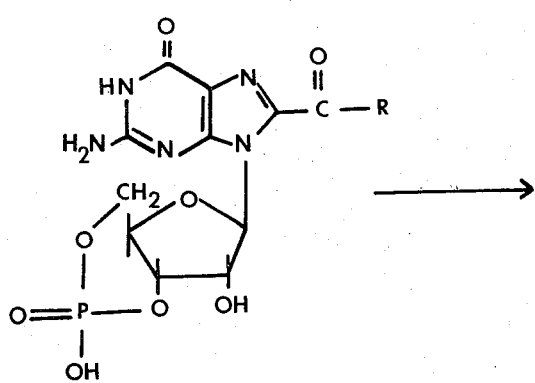
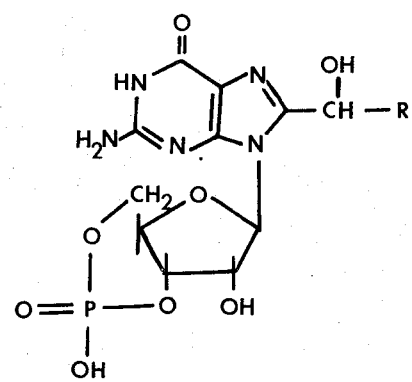
6, R = CH₃
7, R = CH₂CH₂CH₃
8, R = CH(CH₃)₂
9, R = C₆H₅
10, R = NH₂
11, R = CH₃
12, R = CH₂CH₂CH₃
13, R = CH(CH₃)₂
14, R = C₆H₅
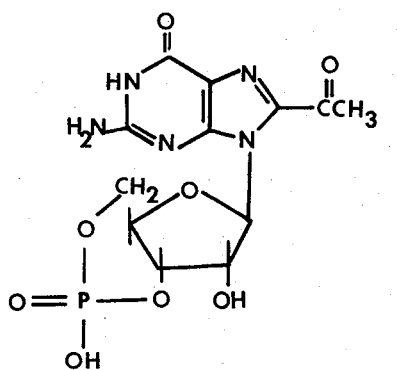
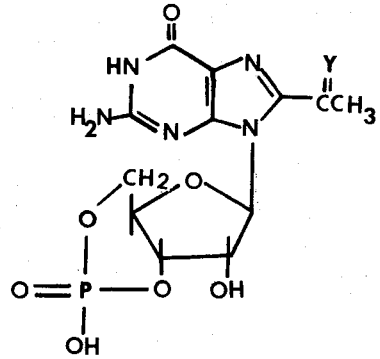
6
15, Y = N-NH-C(=S)-NH₂
16, Y = N-NH-C(=O)-NH₂
17, Y = N-NH-C(=O)-NH-C₆H₅
18, Y = N-NH-C₆H₅
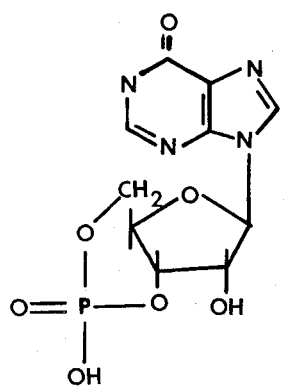
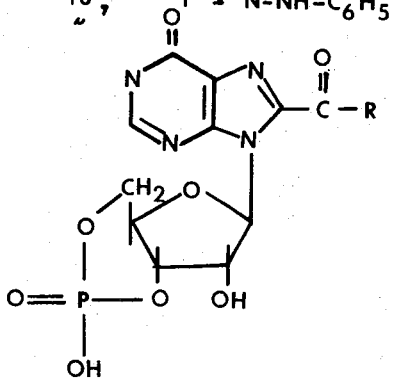
19
20, R = CH₃
21, R = C₆H₅

In the presence of $FeSO_4$, t-butyl hydroperoxide decomposes to yield acetone and the methyl radical (Minisci, et al, 1971, *Tetrahedron* 27, 3575). When cGMP (1) was treated with these reagents in 0.3 N $H_2SO_4$ solution, 8-methylguanosine 3',5'-cyclic phosphate (2) was isolated in 75% yield. Compound 2 was characterized by the uv spectra, which was similar to cGMP, and the absence of the C-8 proton in the pmr. Although it might be expected that cleavage might result in the cyclic phosphate or ribosyl moieties under these conditions, no chromatograhic evidence was found for such cleavage.

Treatment of cGMP with trimethylhydroperoxypentane under the conditions used for the synthesis of 2 gave 8-neopentylguanosine 3',5'-cyclic phosphate (5) in 16% yield. A benzyl radical was generated from toluene, in situ with cGMP in aqueous acetic acid with $FeSO_4$ and ammonium persulfate radical initiator to give 8-benzylguanosine 3',5'-cyclic phosphate (4) in 6% yield.

Hydrogen abstraction from the carbonyl carbon of aldehydes by a radical source was utilized to yield the acyl radical, a highly reactive acylating agent, for the synthesis of 8-acyl-cGMP derivatives. Acetaldehyde and cGMP, in the presence of t-BuOOH, $FeSO_4$ and 0.3 N $H_2SO_4$, yielded 8-acetylguanosine 3',5'-cyclic phosphate (6); however, in initial experiments a significant amount of 8-methyl-cGMP (2) was also formed. To avoid the possibility of methylation competing with hydrogen abstraction from the aldehyde, ammonium persulfate was subsequently used as a radical source. In this manner, 6 was readily obtained in 43% yield. Using the appropriate aldehyde under these conditions, 8-n-butyryl (7), 8-isobutyryl (8), and 8-benzoylguanosine 3',5'-cyclic phosphate (9) were prepared from cGMP. Formamide and cGMP under these conditions gave 8-carbamoylguanosine 3',5'-cyclic phosphate (10).

Side reactions were minimal in the homolytic acylation reaction with one exception. Isobutyraldehyde and cGMP gave 8 in 47% yield, but tlc revealed another component in addition to unreacted cGMP. This product was isolated in 22% yield and identified as 8-isopropylguanosine 3',5'-cyclic phosphate (3), obtained presumably by partial decarbonylation of the isobutyryl radical.

The novel 8-acyl-cGMP derivatives were shown to undergo the usual reactions characteristic of ketones. Treatment of 6—9 with $NaBH_4$ in water readily gave 8-(1-hydroxyethyl)-(11), 8-(1-hydroxybutyl)-(12), 8-(1-hydroxy-2-methylpropyl)-(13), and 8-($\alpha$-hydroxybenzyl)guanosine 3',5'-cyclic phosphate (14), respectively. Compound 6 also yielded a thiosemicarbazone (15), semicarbazone (16), 4-phenylsemicarbazone (17), and phenylhydrazone (18) upon treatment with the appropriate reagent in water.

The structures of the 8-acyl-cGMP derivatives were assigned by the pmr spectra, which showed the expected new peaks of the substituent in addition to the loss of the C-8 proton. In all cases the anomeric proton appeared as an apparent singlet, verifying the integrity of the cyclic phosphate ring. The uv spectra maxima and tlc data are given in Table I.

Table I

Physical Properties of 8-Substituted cGMP Derivatives.

| No. | $\lambda_{max}$ (nm)($\epsilon \times 10^{-3}$) pH 1 | pH 7 | pH 11 | $R_{cGMP}^a$ A | B | Solvent$^c$ | H—1' | $\delta$, ppm$^d$ (8-Substituent) |
|---|---|---|---|---|---|---|---|---|
| 2 | 260(13.3) | 252(13.8) | 257(13.2) | 1.0 | 1.1 | I | 5.83 | 2.56(s,3) |
| 3 | 261(15.1) | 253(15.6) | 258(14.7) | 1.8 | 1.9 | I | 5.96 | 1.37(d,6), 3.30(m,1) |
| 4 | 262(16.2) | 256(18.0) | 262(16.2) | 2.1 | 2.4 | I | 5.77 | 2.51(s,2), 7.34(s,5) |
| 5 | 262(15.7) | 256(17.4) | 259(15.7) | 1.9 | 1.7 | II | 5.81 | 1.04(s,9), 2.76(s,2) |
| 6 | 330,276 (16.2,8.1) | 330,276 (16.2,7.9) | 349(17.6) | 2.2 | 1.8 | II | 6.69 | 2.63(s,3) |
| 7 | 331,277 (15.8,7.6) | 332,277 (16.1,7.6) | 350(16.8) | 2.9 | 2.4 | I | 6.77 | 0.99(t,3), 1.7(m,2) |
| 8 | 330,275 (16.2,7.8) | 331,275 (16.3,7.8) | 348(17.0) | 3.0 | 2.6 | I | 6.79 | 1.24(d,6) |
| 9 | 351,271 (14.9,13.4) | 352,271 (14.7,13.1) | 375,253 (16.1,16.1) | 3.1 | 2.6 | II | 6.56 | 7.6(m,3), 8.1(m,2) |
| 10 | 300,275 (14.2,14.8) | 300,275 (14.1,14.3) | 312(15.1) | 1.3 | 1.3 | II | 6.91 | 6.2(bs,2,exchangeable with $D_2O$) |
| 11 | 261(14.8) | 257(16.8) | 262(14.3) | 1.2 | 1.4 | I | 6.19 | 1.69(d,3) |
| 12 | 261(15.8) | 257(17.1) | 262(15.3) | 1.8 | 2.1 | II | 6.22 | |
| 13 | 262(15.4) | 258(17.6) | 262(15.3) | 1.9 | 2.1 | | | |
| 14 | 262(21.0) | 258(23.1) | 267(20.3) | 2.2 | 2.2 | | | |
| 15 | 335,282 (32.2,12.5) | 334,283 (32.6,13.0) | 347,275 (29.2,9.5) | 1.9 | 2.1 | | | |
| 16 | 317(23.0) | 314(24.9) | 324(22.7) | 1.0 | 1.8 | | | |
| 17 | 318(26.9) | 317(28.4) | 327(25.4) | 2.1 | 2.6 | | | |
| 18 | 373,287 (26.4,8.9) | 347,292 (30.2,13.3) | 350(30.2) | 3.1 | 1.7 | | | |
| 20 | 297(7.6) | 297(7.6) | 321(7.0) | 1.6$^b$ | 1.2$^b$ | II | 6.82 | 2.72(s,3), 8.29(s,1,H—2) |
| 21 | 310,269,227 (12.2,11.5,11.1) | 310,269,227 (12.2,11.5,11.0) | 341,265 (9.5,11.5) | 3.9$^b$ | 2.4$^b$ | II | 6.50 | 7.7(b,3), 8.15(m,2), 8.30(s,1,H—2) |

$^a R_{cGMP}$ = Mobility of compound/mobility of cGMP
$^b R_{cIMP}$
$^c$Solvent I = $D_2O$, II = DMSO-$d_6$
$^d$Downfield from internal DSS. H—1' is an apparent singlet in all cases. J = 7 Hz for the split $CH_3$ groups.

Under the conditions employed, there was no evidence for the methylations or acetylations of cAMP.

Inosine 3',5'-cyclic phosphate (19), however, proved to be a substrate for acylation, as noted by the formation of 8-acetyl-(20) and 8-benzoylinosine 3',5'-cyclic phosphate (21) from cIMP and acetaldehyde and benzaldehyde, respectively, in dilute acid with $(NH_4)_2S_2O_8$ and $FeSO_4$. In each case, however, the yield (11 and 1.5%, respectively) was considerably lower than with the corresponding cGMP derivative.

Compounds 20 and 21 were confirmed as 8-substituted inosines by a deuterium exchange experiment. The 8-proton of cIMP exchanges with deuterium when heated at 80° for 1 hr. in $D_2O$ containing NaOD (Bullock and Jardetzky, 1964, *J. Org. Chem.* 29, 1988). The pmr spectra of 20 and 21 showed signals corresponding to one purine C-H proton. Treatment of 20 and 21 with $D_2O$ under conditions which gave complete exchange of the 8-proton of cIMP had no effect on these pmr signals. They therefore correspond to H-2 and the acyl substitutent is at the 8-position of 20 and 21.

EXAMPLES

Tlc samples were dissolved in 0.1 N $NH_4OH$ and developed on Woelm silica gel F-254 plates with either solvent system A ($CH_3CN$-0.1 N $NH_4Cl$,8:2), or B (n-BuOH-HOAc-$H_2O$, 5:2:3). Evaporations were performed under diminished pressure at <40°. Compounds were desalted by absorption on charcoal (Barnebey-Cheney UU, 50–200 mesh), washing with water, and elution with $H_2O$—EtOH—$NH_4OH$ (50:45:5). Chromatography on Dowex 50-X2 (100–200 mesh, $H^+$) resin was performed on a standard 4.5 × 75 cm column unless otherwise stated. Column eluates were monitored at 254 and 313 nm. The ultraviolet spectra reported in Table I were determined on a Cary 15 spectrometer. Elemental analysis were performed by Galbraith Laboratories, Knoxville, Tenn. Pmr spectra in $Me_2SO$-$d_6$ or $D_2O$ were recorded on a Hitachi-Perkin Elmer R-60A with DSS as the internal reference and are reported in Table I.

EXAMPLE 1

8-Methylguanosine 3',5'-Cyclic Phosphate (2)

To a precooled (10°) solution of cGMP.Na.$4H_2O$ (1, 15 g, 34.1 mmol) in 3000 ml 0.3 N $H_2SO_4$ were added simultaneously and dropwise, solutions of $FeSO_4$.$7H_2O$(56.8 g, 204 mmol, in 340 ml of $H_2O$) and t-butyl hydroperoxide (t-BuOOH) (10.9 ml, 136 mmol, in 340 ml of $H_2O$). Addition required 1.5 hr, after which the stirring was continued 0.5 hr. The mixture was then desalted using a column containing 400 ml of charcoal. The eluate was evaporated, then diluted to 100 ml with $H_2O$. A 5 ml aliquot was applied to a Dowex 50-X2 (100–200 mesh, $H^+$) column (4.5 × 75 cm) and eluted with water. Two major bands eluted from the column, the first corresponded to cGMP and the second to 2. This second fraction was evaporated and the resulting solid suspended in $Me_2CO$, filtered, and air dried to give 480 mg (75%) of 2.

Anal. Calcd for $C_{11}H_{14}N_5O_7P.0.5H_2O$: C, 35.87; H, 4.10; N, 19.01. Found: C, 35.67; H, 4.24; H, 18.77.

EXAMPLE 2

8-Acetylguanosine 3',5'-Cyclic Phosphate (6)

cGMP.Na.$4H_2O$ (1, 2.0 g, 4.54 mmol) was dissolved in 100 ml of $H_2O$, then diluted with 100 ml HOAc and 25 ml 3 N $H_2SO_4$. The solution was cooled to 10° and 12 ml of acetaldehyde was added. Separate solutions of $FeSO_4$.$7H_2O$ (10 g, 36 mmol in 60 ml $H_2O$) and $(NH_4)_2S_2O_8$ (8.22 g, 36 mmol in 60 ml $H_2O$) were added simultaneously over 1 hr; stirring was continued an additional 0.5 hr. The solution was diluted with 300 ml $H_2O$ and desalted on charcoal (60 ml). After elution and evaporation, the Residue in a small amount of $H_2O$ was applied to a Dowex 50-X2 (100–200 mesh, $H^+$) column (4.5 × 75 cm) and eluted with water. Monitoring the eluate at 254 and 313 nm showed two close moving bands. The fractions corresponding to the first band, which absorbed at both wavelengths, were combined and evaporated. The residue was suspended in MeOh, filtered and dried in vacuo at 80° to give 808 mg (43%).

Anal. Calcd for $C_{12}H_{14}N_5O_8P$ 1.75$H_2O$: C, 34.41; H, 4.21; N, 16.72. Found: C, 34.07; H, 3.94; N, 16.95.

Recrystallization of the residue from the charcoal column eluate from $H_2O$ gave the $NH_3$ salt of 6 suitable for further transformation.

EXAMPLE 3

8-Butyrylguanosine 3',,5'-cyclic phosphate (7) was synthesized as per the preparation of 6 using 10 g (22.7 mmol) of 1 and 50 ml of butyraldehyde. After desalting on charcoal 4.04 g (36%) of slightly contaminated ammonium salt of 7 was obtained by crystallization from $H_2O$. Passage of the filtrate through Dowex 50-X2 column gave, after evaporation and suspension of the residue in acetone, 3.42 g (34%) of pure 7. For analysis a small amount of the ammonium salt was passed through Dowex 50-X2, and the residue after evaporation was suspended in acetone, filtered, and dried in vacuo at 80° for 18 hr.

Anal. Calcd for $C_{14}H_{18}N_5O_8P.1.5H_2O$: C, 38.02; H, 4.79; N, 15.83. Found: C, 38.13; H, 4.64; N, 15.77.

EXAMPLE 4

8-Isobutyrylguanosine 3',5'-Cyclic Phosphate Ammonium Salt (8) and 8-Isopropylguanosine 3',5'-Cyclic Phosphate (3)

Compound 8 was prepared as per 6, using 10 ml of 2-methyl-1- propanal and 2 g (4.55 mmol) of 1. After elution from the Dowex 50-X2 column the fractions corresponding to the first major band were evaporated with an excess $NH_4OH$ to give 0.98 g (47%) of 8.

Anal. Calcd for $C_{14}H_{18}N_5O_8P.NH_3$1.5$H_2O$: C, 36.61; H, 5.27; N, 18.30. Found: C, 36.84; H, 5.29; N, 17.92.

Unreacted 1 eluted from the Dowex 50-X2 column immediately after 8. Continued elution with water produced another major band having uv absorption at 254 nm but not at 313. The fractions corresponding to this band were evaporated and the residue was suspended in methanol to give 3. In a reaction using 10 g (22.7 mmol) of 1 the yield of 3 was 2.11 g (22%) after drying in vacuo at room temperature.

Anal. Calcd for $C_{13}H_{18}N_5O_7P.2H_2O$: C, 36.89; H, 5.24; N, 16.54. Found: C, 36.64; H, 5.58; N, 16.42.

EXAMPLE 5

8-Benzoylguanosine 3',5'-cyclic phosphate (9) was prepared as per 6 using benzaldehyde (100 ml) and 10 g (22.7 mmol) of 1. The reaction mixture was evaporated; the residue was triturated with $Et_2O$, then $H_2O$. The residue was stirred in $H_2O$ (800 ml) while the pH was adjusted to 8 using 2 N NaOH. The filtered solution was adjusted to pH 1.5 with conc HCl, diluted to 2 l. with $H_2O$, and applied to an Amberlite XAD-4 column (4 × 70 cm, 850 ml). The column was washed with several liters of $H_2O$ and then with a 12 l. gradient from 0% to 75% MeOH in $H_2O$. The fractions corresponding to the major band eluting from the column were evaporated; the residue was dissolved in 100 ml MeOH and dropped into 1000 ml $Et_2O$. The resulting solid was filtered and dried in vacuo at room temperature to give 1.5 g (14%) of 9.

Anal. Calcd for $C_{17}H_{16}N_5O_8P$: C, 45.44; H, 3.58; N, 15.58. Found: C, 45.16; H, 3.70; N, 15.44.

EXAMPLE 6

8-Carbamoylguanosine 3',5'-Cyclic Phosphate (10)

To a stirred solution of 1 (10 g, 22.7 mmol) in 500 ml H$_2$O was added 500 ml HOAc, 50 ml 3N H$_2$SO$_4$ and 100 ml formamide. After cooling to 10° 100 g of FeSO$_4$.7H$_2$O was added. A solution of 82.2 g of (NH$_4$)$_2$S$_2$O$_8$ in 300 ml H$_2$O was then added dropwise over 0.75 hr followed by stirring an additional 0.5 hr. After workup as for 6, the product was crystallized from H$_2$O at 0°. Filtration and drying in vacuo at room temperature gave 6.1 g (63%) of 10.

Anal. Calcd for C$_{11}$H$_{13}$N$_6$O$_8$P.2H$_2$O: C, 31.14; H, 4.04; N, 19.80. Found: C, 31.02; H, 3.85; N, 18.20.

EXAMPLE 7

8-(1-Hydroxyethyl)guanosine 3',5'-Cyclic Phosphate (11)

Compound 6, ammonium salt (5.0 g, 10.5 mmol), was stirred in H$_2$O(75 ml) with NaBH$_4$(400mg, 10.5 mmol) for 0.5 hr. The pH was adjusted to 2 with conc HCl and the solution was then desalted using a charcoal column (100 ml). The eluate was evaporated, the residue was dissolved in 125 ml MeOH$_5$, and an equal volume of Et$_2$O was added. The resulting solid was filtered and dried in vacuo at room temperature to give 3.10 g (69%) of the ammonium salt of 11. For analysis, a portion was passed through a Dowex 50-X8 column in water. The fractions containing product were evaporated, and the residue was triturated with MeOH and dried in vacuo at room temperature.

Anal. Calcd for C$_{12}$H$_{16}$N$_5$O$_8$P.2H$_2$O: C, 33.89; H, 4.74; N, 16.47. Found: C, 33.99; H, 4.86; N, 16.08.

EXAMPLE 8

8-(1-Hydroxybutyl)guanosine 3',5'-Cyclic Phosphate (12)

One gram (2.26 mmol) of 7 was treated with NaBH$_4$ as for 11. After acidification the solution was passed through a Dowex 50-X2(100–200 mesh, H$^+$)column(4.5×70cm). The fractions corresponding to product were evaporated, dissolved in a small amount of MeOH and dropped into Et$_2$O(200 ml). The moist solid was collected on a filter and dried in vacuo at room temperature to give 846 mg of 12. An analytical sample was recrystallized from MeOH-EtOH.

Anal. Calcd for C$_{14}$H$_{20}$N$_5$O$_8$P.2H$_2$O: C, 37.09; H, 5.34; N, 15.45. Found: C, 36.81; H, 5.16; N. 15.38.

EXAMPLE 9

8-(1-Hydroxy-2-methylpropyl)guanosine 3',5'-Cyclic Phosphate (13)

Compound 8 (500 mg, 1.03 mmol, ammonium salt) was reduced as in synthesis of 11. After desalting on charcoal the residue was passed through a Dowex 50-X2 column and eluted with H$_2$O. The appropriate fractions were evaporated to dryness, and the residue was suspended in Me$_2$CO, filtered, and dried in vacuo at room temperature to give 158 mg(33%) of 13.

Anal. Calcd for C$_{14}$H$_{20}$N$_5$O$_8$P.2.5H$_2$O: C, 36.37; H, 5.45; N, 15.15. Found: C, 35.88; H, 5.38; N, 15.43.

EXAMPLE 10

8-(α-Hydroxybenzyl)guanosine 3',5'-Cyclic Phosphate (14)

Compound 9(100 mg, 0.22 mmol) was treated with NaBH$_4$(60 mg) in 2 ml H$_2$O for 0.5 hr. The pH was adjusted to 1 with 1 N HCl. The resulting crystals were filtered and air dried to give 65 mg(59%). For analysis a portion was passed through a short silica gel column eluting with 30% MeOH in CHCl$_3$. After evaporation the residue was suspended in 1 N HCl, filtered, washed with water and dried in vacuo.

Anal. Calcd for C$_{17}$H$_{18}$N$_5$O$_8$P.3H$_2$O: C, 40.40; H, 4.79; N, 13.86. Found: C, 40.50; H, 4.43; N, 13.73.

EXAMPLE 11

8-Acetylguanosine 3',5'-Cyclic Phosphate Thiosemicarbazone (15)

Compound 6 (840 mg, 2 mmol) and thiosemicarbazide (180 mg, 2 mmol) in water (10 ml) were heated on steam bath for 1 hr. After cooling the solid was filtered and dried in vacuo at 80° to give 690 mg (59%) of 15.

Anal. Calcd for C$_{13}$H$_{17}$N$_8$O$_7$PS.2.5H$_2$O: C, 30.89; H, 4.39; N, 22.17. Found: C, 30.79; H, 4.49; N, 21.79.

EXAMPLE 12

Compounds 16, 17 and 18 were prepared from compound 6 via the process of Example 11 using the appropriate hydrazine derivative.

a. 8-Acetylguanosine 3',5'-Cyclic Phosphate Semicarbazone (16); yield 81%.

Anal. Calcd for C$_{13}$H$_{17}$N$_8$O$_8$P.1.5H$_2$O: C, 33.12; H, 4.27; N, 23.77. Found: C, 32.94, H, 4.01; N, 23.54.

b. 8-Acetylguanosine 3',5'-Cyclic Phosphate 4-Phenylsemicarbazone (17); yield 84%.

Anal. Calcd for C$_{19}$H$_{21}$N$_8$O$_8$P.3H$_2$O: C, 39.73; H, 4.74; N, 19.51. Found: C, 39.97; H, 4.71; N, 19.79.

c. 8-Acetylguanosine 3',5'-Cyclic Phosphate Phenylhydrazone (18); yield 95%.

Anal. Calcd for C$_{18}$H$_{20}$N$_7$O$_7$P.2.5H$_2$O: C, 41.38; H, 4.82; N, 18.76. Found: C, 41.11; H, 5.13; N, 18.46.

EXAMPLE 13

8-Benzylguanosine 3',5'-Cyclic Phosphate (4)

Compound 4 was synthesized as per the preparation of 6 using 4.0 g(9.1 mmol) of 1 and 20 ml of toluene. The reaction mixture was evaporated to dryness and the residue taken up in H$_2$O for desalting. The eluate from charcoal was evaporated, and the residue, in 100 ml H$_2$O, was passed in two portions through a Dowex 50-X2 column and eluted with water. Two major bands emerged from the column, the first corresponding to 1 and the second to 4. The appropriate fractions were condensed to a small volume. The crystalline product was filtered and dried in vacuo at room temperature to give 250 mg (6%) of 4.

Anal. Calcd for C$_{17}$H$_{18}$N$_5$O$_7$P$_1$.2H$_2$O: C, 43.32; H, 4.70; N, 14.86. Found: C, 43.14; H, 4.58; N, 14.75.

EXAMPLE 14

8-Neopentylguanosine 3',5'-Cyclic Phosphate (5)

To a solution of 1 (2.0 g, 4.54 mmol) and FeSO$_4$.7H$_2$O (6.3 g, 22.7 mmol) in H$_2$O (100 ml) was added HOAc (100 ml) and 3 N H$_2$SO$_4$ (25 ml). The mixture was cooled to 5°–10° with some solid precipitate resulting. 2,4,4-Trimethyl-2-hydroperoxypentane (3.32 g, 22.7 mmol) (Hoffman, 1960, Org. Syn., 40, 76) was added dropwise with vigorous stirring over 0.5 hr after which the stirring continued 0.5 hr. The solution was evaporated then redissolved in water (1000 ml) and desalted on charcoal (50 ml). After evaporation of the appropriate fractions, the residue was dissolved in a small amount of water and applied to Dowex 50-X2 column and eluted with water. Fractions containing cGMP eluted first. These were evaporated and suspended in acetone to give cGMP (890 mg, 2.5 mmol). The second uv absorbing band eluting from the column contained 5. These fractions were evaporated, dissolved in 15 ml 1 N NH$_4$OH, filtered and adjusted to pH 1 with conc HCl. After several hours, the crystals were filtered, washed with water and dried in vacuo at room temperature to give 345 mg (16%, or 35% based on unrecovered 1) of 5.

Anal. Calcd for $C_{15}H_{22}N_5O_7P.3.5H_2O$: C, 37.66; H, 6.11; N, 14.64. Found: C, 37.63; H, 5.90; N, 14.51.

EXAMPLE 15

8-Acetylinosine 3',5'-Cyclic Phosphate (20)

To a solution of 3.0 g (8.6 mmol) inosine 3',5'-cyclic phosphate (19, Meyer, et al., 1972, Biochemistry 11, 2704) and 25 ml acetaldehyde in 300 ml 0.3 N H$_2$SO$_4$ at 10° were added simultaneously and dropwise, 30 g FeSO$_4$.7H$_2$O in 180 ml H$_2$O and 24.7 g (NH$_4$)$_2$S$_2$O$_8$ in 180 ml H$_2$O. After 0.5 hr additional stirring, the solution was desalted. To the residue from evaporation of the charcoal eluate was added aqueous alcohol and 6 g silica gel. The solvent was evaporated and the dried residue was added to the top of a silica gel column (60g), packed in and eluted with 30% MeOH in CHCl$_3$. Product appeared first from the column, followed by 19. Appropriate product-containing fractions were pooled and evaporated, and the residue was dissolved in H$_2$O and passed through Dowex 50(H$^+$). Evaporation of the eluate and trituration of the residue with Me$_2$CO gave 430 mg (11%).

Anal. Calcd for $C_{12}H_{13}N_4O_8P.3H_2O$: C, 33.81; H, 4.49; N, 13.14. Found: C, 34.04; H, 4.52; N, 13.30.

EXAMPLE 16

8-Benzoylinosine 3',5'-Cyclic Phosphate (21)

Compound 21 was synthesized in a manner similar to 6 using 10.0 g (28.6 mmol) 19 and benzaldehyde. After desalting the residue was dissolved in H$_2$O and applied to an Amberlite XAD-4 column (4 × 70 ml, 800 ml). The column was washed with H$_2$O then eluted with a 6 l. gradient from 0% to 75% MeOH in H$_2$O. The fractions corresponding to the major band eluting near the end of the gradient were evaporated. The residue was dissolved in H$_2$O and passed through a Dowex 50 (H$^+$) column. Evaporation of the eluate gave 205 mg (1.5%) of 21 after drying in vacuo at room temperature.

Anal. Calcd for $C_{17}H_{15}N_4O_8P.1.5H_2O$: C, 44.26; H, 3.92; N, 12.14. Found: C, 44.35; H, 3.83; N, 12.20.

EXAMPLE 17

The new 8-substituted purine cyclic nucleotides were examined for their ability to stimulate both a cAMP-dependent protein kinase isolated from beef brain and a cGMP-dependent protein kinase isolated from lobster tail (see Table II). The intracellular action of both cAMP and cGMP has been postulated (Kuo and Greengard, 1969, Proc. Nat. Acad. Sci. USA 64, 1349, Kuo et al, 1971, J. Biol. Chem. 246,7159) to be mediated by its activation of a protein kinase.

The K$_a$ of cAMP for the cAMP-dependent protein kinase is about the same (see footnote a, Table II) as the K$_a$ of cGMP for the cGMP-dependent protein kinase. Comparison of the K$_a$' values (the ratio of K$_a$ of the dependent cyclic nucleotide to the K$_a$ of the test compound) is, therefore, an accurate guide to the type of kinase stimulation seen at a given cyclic nucleotide concentration.

The 8-acyl and 8-alkyl cGMP derivatives reported here showed a remarkable specificity for the cGMP-dependent enzyme, as shown in Table II.

Table II

Activation of Protein Kinase and Inhibition of Phosphodiesterase Activity by the 8-Substituted Derivatives of cGMP and cIMP.

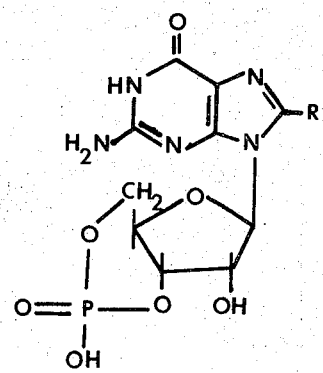

| Compound No. | R | Protein Kinase,[a] K$_a$' Bovine | Lobster | Phosphodiesterase Inhibition,[b] I$_{50}$,μM Lung | Heart |
|---|---|---|---|---|---|
| 1 | H | 0.023 | 1.0 | | |
| 2 | CH$_3$ | 0.015 | 0.066 | 400 | 200 |
| 3 | CH(CH$_3$)$_2$ | <0.001 | 0.70 | 330 | 100 |
| 4 | CH$_2$C$_6$H$_5$ | <0.001 | 0.10 | 130 | 140 |
| 5 | CH$_2$C(CH$_3$)$_3$ | <0.001 | 0.16 | 70 | 100 |
| 6 | COCH$_3$ | <0.001 | 0.56 | 70 | 170 |
| 7 | COC$_3$H$_7$ | 0.064 | 0.20 | 70 | 90 |

Table II -continued

Activation of Protein Kinase and Inhibition of Phosphodiesterase Activity by the 8-Substituted Derivatives of cGMP and cIMP.

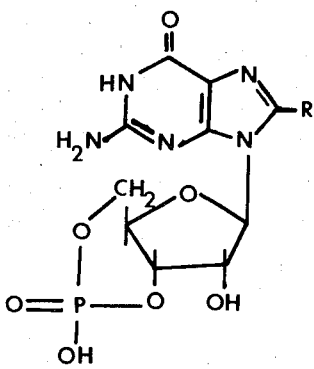

| Compound No. | R | Protein Kinase,[a] $K_a'$ Bovine | Lobster | Phosphodiesterase Inhibition,[b] $I_{50},\mu^M$ Lung | Heart |
|---|---|---|---|---|---|
| 8 | COCH(CH$_3$)$_2$ | <0.01 | 0.13 | 50 | 11 |
| 9 | COC$_6$H$_5$ | <0.005 | 0.68 | 50 | 50 |
| 10 | CONH$_2$ | <0.001 | 1.5 | 400 | 100 |
| 11 | CHOHCH$_3$ | <0.01 | 1.8 | 400 | 170 |
| 12 | CHOHC$_3$H$_7$ | <0.001 | 0.62 | 133 | 29 |
| 13 | CHOHCH(CH$_3$)$_2$ | <0.001 | 0.72 | 180 | 38 |
| 14 | CHOHC$_6$H$_5$ | <0.005 | 2.3 | 140 | >300 |
| 15 | C(NNHCSNH$_2$)CH$_3$ | <0.005 | 0.052 | 26 | 50 |
| 16 | C(NNHCONH$_2$)CH$_3$ | <0.005 | 0.031 | 200 | 125 |
| 17 | C(NNHCONHC$_6$H$_5$)CH$_3$ | <0.01 | 0.11 | 150 | 40 |
| 18 | C(NNHC$_6$H$_5$)CH$_3$ | <0.005 | 0.44 | 2000 | 100 |
| 19 | H | 0.59 | 0.085 | 100 | 3.9 |
| 20 | COCH$_3$ | 0.022 | 0.0041 | 2000 | 1000 |
| 21 | COC$_6$H$_5$ | 0.070 | 0.011 | 400 | 70 |

[a] $K_a'$ = The ratio of $K_a$ of the dependent cyclic nucleotide (cAMP for bovine brain and cGMP for lobster tail) to the $K_a$ of the test compound. The $K_a$ of cAMP for the bovine brain kinase is $2.0 \times 10^{-7}$ M and the $K_a$ of cGMP for the lobster tail kinase is $1.7 \times 10^{-7}$ M.

[b] $I_{50}$ is the concentration of test compound necessary for 50% inhibition of the cleavage of cAMP (concentration of cAMP = $1.6 \times 10^{-7}$ M). The $I_{50}$ of theophylline is 200 µM against rabbit lung and 100 µM against beef heart. Only 8-butyryl-cGMP showed even modest ability to stimulate the cAMP-dependent kinase, having a $K_a'$ of 0.064 for this enzyme. None of the other compounds derived from cGMP demonstrated a $K_a'$ better than 0.01 with the cAMP-dependent protein kinase.

When assayed as activators of the cGMP-dependent protein kinase, most of the 8-substituted cGMP's proved to be fair to excellent. The 8-carbamoyl (10), 8-(1-hydroxyethyl) (11) and 8-(α-hydroxybenzyl)-cGMP (14) proved to be superior to cGMP in their ability to activate this kinase.

Generally, the 8-(1-hydroxyalkyl) derivatives 11 - 14 showed exceptional ability to stimulate the kinase. In fact, when each member of Group 3 was compared with its respective member of Group 2 (i.e., 11 with 6, etc.), a constant 3 to 5-fold increase in $K_a'$ was realized upon conversion of the keto function to a hydroxy function. Direct free radical acylation to yield intermediate acyl compounds, with subsequent derivatization of the keto function to give final products with enhanced physiological activity may prove invaluable for the synthesis of highly active nucleotides.

Two 8-acyl-cIMP analogs (compounds 20 and 21) exhibited slight activation of both cGMP and cAMP protein kinases, showing slightly greater specificity for the cAMP-dependent enzyme. This is in agreement with the greater activation of the cAMP-dependent kinase by cIMP itself, and with the preference for the cAMP-dependent enzyme by the other 8-substituted-cIMP derivatives which have been reported, Miller et al, 1973, supra.

All compounds were examined for their susceptibility to hydrolysis by cyclic nucleotide phosphodiesterase. Both cGMP and cIMP were hydrolyzed at approximately one-half the rate of cAMP by a rabbit kidney enzyme preparation generally prepared in the manner described below for rabbit lung enzyme. The new 8-substituted derivatives were not substrates (rate of hydrolysis<0.05 that of the rate of cAMP hydrolysis) within the limits of detection of our assay, with the sole exception of 8-(1-hydroxybutyl)-cGMP (12), which was hydrolyzed at a rate 0.18 times the rate of hydrolysis of cAMP. This finding is in agreement with the general conclusion that 8-substitution of a purine 3',5'-cyclic ribonucleotide greatly reduces the ability of the resulting derivative to serve as a substrate for cyclic nucleotide phosphodiesterase.

All of the compounds reported herein were also examined for their ability to inhibit the hydrolysis of cAMP by both rabbit lung and beef heart cyclic nucleotide phosphodiesterase, as is shown in Table II. Homogenates of rabbit lung and beef heart are made in sucrose-Tris-magnesium buffer and are subjected to centrifugation at low speed to remove nuclei and cell debris. The supernatants are then centrifuged at 105,000 × g for 30 minutes, and the 105,000 × g supernatants are then fractionated using (NH$_4$)$_2$SO$_4$. The precipitation which forms at 0–50% saturation is collected by centrifugation at 20,000 × g, dissolved in Tris-magnesium buffer, and dialyzed overnight against the same buffer. The second $(NH_4)_2SO_4$ fraction was then assayed for PDE activity using the method of Appleman, *Biochem.* 10, 311 (1971).

Some of the compounds inhibited the rate of cAMP hydrolysis by 50% at concentrations in the $10^{-5}$ to $10^{-4}$ range, within the same order of magnitude as was observed for the 8-bromo,8-thio,and 8-amino derivatives of cBGMP previouslyreported, Miller, et al, 1973, supra. As was the case with the latter compounds, Miller et al, 1973, supra, the 8-alkyl and 8-acyl-cGMP derivatives reported here were competitive inhibitors of the enzyme.

The remarkable specificity shown by the 8-alkyl and 8-acyl cGMP-derivatives for the cGMP-dependent protein kinase, coupled with their apparent lack of hydrolysis by phosphodiesterase, indicates that this class of compounds is very useful in effecting biological responses involving cGMP.

We claim:

1. The compound of the structure:

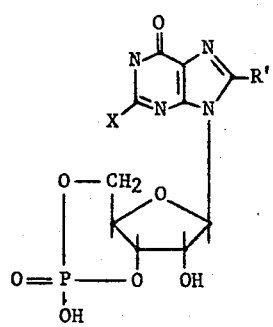

wherein X is H or $NH_2$; and R' is iso-propyl; neo-pentyl; $C_1$ to $C_8$ substituted alkyl wherein the alkyl is substituted at the 1-alkyl position and the substituents are selected from the group consisting of hydroxyl, phenyl, semicarbazone, thiosemicarbazone, 4-phenyl semicarbazone, and phenyl hydrazone; benzyl; $C_1$ to $C_8$ acyl; or carbamoyl.

2. The compound of the structure:

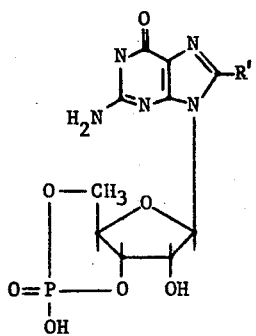

wherein R' is iso-propyl; neo-pentyl; $C_1$ to $C_8$ substituted alkyl wherein the alkyl is substituted at the 1-alkyl position and the substituents are selected from the group consisting of hydroxyl, phenyl, semicarbazone, thiosemicarbazone, 4-phenyl semicarbazone, and phenyl hydrazone; benzyl; $C_1$ to $C_8$ acyl; or carbamoyl.

3. The compound 8-butyrylguanosine 3',5'-cyclic phosphate.

4. The compound 8-benzoylguanosine 3',5'-cyclic phosphate.

5. The compound 8-carbamoylguanosine 3',5'-cyclic phosphate.

6. The compound 8-(1-hydroxyethyl)guanosine 3',5'-cyclic phosphate.

7. The compound 8-(α-hydroxybenzyl)guanosine 3',5'-cyclic phosphate.

8. The compound of the structure:

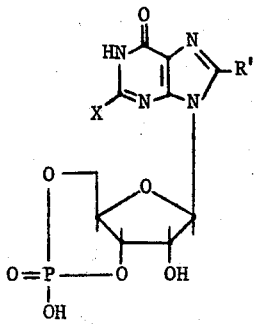

wherein R' is $C_1$ to $C_8$ alkyl; $C_1$ to $C_8$ substituted alkyl wherein the alkyl is substituted at the 1-alkyl position and the substituents are selected from the group consisting of hydroxyl, phenyl, semicarbazone, thiosemicarbazone, 4-phenyl semicarbazone and phenyl hydrazone; benzyl; $C_1$ to $C_8$ acyl; or carbamoyl.

9. The compound 8-acetylinosine 3',5'-cyclic phosphate.

10. The compound 8-Benzoylinosine 3',5'-cyclic phosphate.

11. A process of synthesizing 8-substituted 3',5'-cyclic phosphate nucleotides of the general formula:

wherein X is H or $NH_2$ and R' is iso-propyl, neo-pentyl, benzyl, $C_1$ to $C_8$ acyl or carbamoyl comprising reacting the corresponding 8 unsubstituted nucleotide with a free radical corresponding to R' generated in situ from an alkyl peroxide, an aldehyde, formamide or toluene in the presence of $Fe^{++}$ and either a persulfate or alkyl peroxide free radical initiator with the proviso that when R' is generated from the alkyl peroxide the alkyl peroxide can serve as both the R' source and the free radical initiator.

12. The process of claim 11 wherein the iso-propyl and neo-pentyl free radicals are generated in situ with the nucleotide via reaction between $Fe^{++}$ and the corresponding alkyl peroxide.

13. The process of claim 12 wherein the alkyl peroxide is t-butyl peroxide or trimethylhydroperoxypentane.

14. The process of claim 11 wherein the benzyl free radical is generated in situ with the nucleotide via reaction between $Fe^{++}$, toluene and a free radical initiator.

15. The process of claim 11 wherein the $C_1$ to $C_8$ acyl free radical is generated in situ with the nucleotide via hydrogen abstraction of the carbonyl carbon of an aldehyde by a free radical source.

16. The process of claim 15 wherein the free radical source is generated via the reaction between $Fe^{++}$ and a free radical initiator selected from the group consisting of t-butyl peroxide and ammonium persulfate.

17. A process of synthesizing 8-(1-substituted)purine of the general formula:

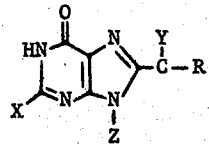

wherein X is H or $NH_2$; Z is selected from the group consisting of 9-β-D-ribofuranosyl, 9-β-D-ribofuranosyl 3',5'-cyclic phosphate, and 9-β-D-ribofuranosyl 5'-phosphate; R is selected from the group consisting of $C_1$ to $C_8$ alkyl, phenyl, and benzyl; and Y is selected from the group consisting of hydroxy, semicarbazone, thiosemicarbazome, 4-phenyl semicarbazone, and phenyl hydrazone comprising reacting a compound of the structure:

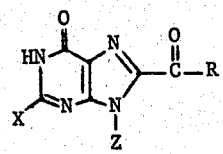

wherein X, Z, and R are the same as above with $NaBH_4$, hydrazine, semicarbazide, thiosemicarbazide, 4-phenyl semicarbazide, or phenyl hydrazine.

* * * * *